United States Patent [19]
Alam et al.

[11] Patent Number: 5,252,602
[45] Date of Patent: Oct. 12, 1993

[54] EFFECTS OF MISOPROSTOL ON ALLERGIC RESPONSES

[76] Inventors: Rafeul Alam, 14910 Wilderness Cliff, Houston, Tex. 77062; J. Andrew Grant, 2914 Beluche St., Galveston, Tex. 77551

[21] Appl. No.: 774,664

[22] Filed: Oct. 11, 1991

[51] Int. Cl.$^5$ .......................................... A61K 31/215
[52] U.S. Cl. .................................. 514/530; 514/573; 514/826
[58] Field of Search ..................... 514/530, 573, 826

[56] References Cited

U.S. PATENT DOCUMENTS 4,066,787  1/1978  Okazaki et al. ..................... 514/573

FOREIGN PATENT DOCUMENTS

0399175A3  3/1990  European Pat. Off. .
0494063A2  12/1991  European Pat. Off. .

OTHER PUBLICATIONS

Chemical Abstracts, 81:37324g (1974)–Hayashi.
Chemical Abstracts, 87:84618q (1977)–Bundy.
Chemical Abstracts 104:15172x (1986)–Bauer.
Alam, R. et al., May, 1992, *Amer. Review of Resp. Diseases*, 145(4) (2):A734 "Selective Inhibition of the Cutaneous Late Allergic Response to Dust Mite by Misoprostol, an Orally Active Prostaglandin E Analogue Results of Double-Blind Placebo-Controlled Study".
Dejarnatt, A. C., et al., Jan. 1992, *The J. of Allergy and Clin. Immun.*, 89(1) (2):200, Abst. 221, "Misoprostol (MPL), a PGE Analogue, Inhibits the Late but Not the Immediate Cutaneous Allergic Reaction to Dust Mite Antigens".
Manning, P. J., et al., 1989, *Pulmonary Pharmacology*, 2(3):121–124, "the Effect of Oral Prostaglandin E1 on Airway Responsiveness in Asthmatic Subjects".
Podleksi, W. K., 1989, *Int'l. Jour. of Immunopharm.*, 11(4):311–326, "Pharmacotherapy of Food Allergy-A Neglected Option".
The Patent Cooperation Treaty International Search Report dated Feb. 10, 1993.
Goodman and Gilman, eds., The Pharmacological Basis of Therapeutics, 18th edition (1990), pp. 574–588, p. 610–611, pp. 618–619, and p. 638.
Bauer, R. F. (1985) *Dig. Dis. Sci.*, (USA), Supplement, 30(11):118S–125S.
Merck, Manual (1987) 15th ed., R. Berkow et al., eds., pp. 304–306.
Mark Feldman (1990) *The American Journal of Medical Sciences*, 300(2):116–132.

*Primary Examiner*—Leonard Schenkman

[57] ABSTRACT

Methods for treating and preventing late-phase allergic reactions with misoprostol in a pharmaceutically acceptable excipient are provided. Tablet forms of misoprostol may be administered at doses of between 100 μg and 300 μg. The preparation may be administered alternatively as an aerosol. Late-phase respiratory and cutaneous reactions to dust mites, food and occupational allergens, pollen, weeds, grass, drugs, animal dander and chemicals may be treated with the described misoprostol-containing agents. Urticaria, contact dermatitis, asthma, allergic rhinitis and anaphylaxis are conditions which may be treated according to the presently disclosed methods and pharmaceutical agents.

23 Claims, 7 Drawing Sheets

EFFECTS OF MISOPROSTOL ON ALLERGIC RESPONSES

BACKGROUND OF THE INVENTION

1. Field of the Invention

The present invention relates to the field of methods for treating and preventing late-phase allergic reactions, such as late-phase cutaneous allergic reactions. The present invention also relates to the field of treatments for inflammatory diseases, allergic rhinitis, asthma, contact dermatitis, anaphylaxis, and urticaria. The present invention also relates to the field of pharmaceutical agents, as a pharmaceutical anti-allergy agent for treating a late phase allergic response in an animal is also provided.

2. Description of the Relevant Art

Prostaglandins (PGE) have historically been implicated in the pathogenesis of inflammation. This group of chemical mediators are known to have a variety of diverse functions, including the modulation of inflammatory cells. For example, the E series of prostaglandins inhibits the activity of many inflammatory cells. PGE prevents the synthesis of cytokines by monocytes and blocks the release of mediators from polymorphonuclear cells (PMN) and basophils. They also affect the function of lymphocytes.

PGE has been shown to have many anti-inflammatory and immunomodulatory effects. PGE is known to inhibits the activation of neutrophils, basophils, and monocytes. It also blocks the proliferation of lymphocytes and the expression of IL 2 receptors. PGE is also a strong smooth muscle relaxant and induces bronchodilatation in vivo. The immunomodulatory effect of PGE has been demonstrated by the increased survival of renal allografts in transplant recipients.

Theories surrounding the current understanding of the pathophysiology of allergic diseases has changed significantly in recent years. Initially considered as a disorder of mast cells, it is now increasingly recognized as a chronic inflammatory disease. The involvement of eosinophils, lymphocytes, basophils, monocytes/macrophages and neutrophils has also been recently appreciated.

It is believed that cytokines and interleukins released by activated lymphocytes and macrophages attract other inflammatory cells. "Mediators" of inflammation, of which there are many, are released by eosinophils, basophils and other effector cells, and induce a chronic inflammation that is reminiscent of chronic asthma and other allergic disorders.

An important development in the area of allergic diseases has been the recognition of a "late-phase" allergic reaction that follows approximately 2–12 hours after an immediate "early-phase" allergic reaction, which is separately characterizable both in sequence of onset and differences in appearance and general severity of symptoms. Morphologic studies have demonstrated the infiltration of eosinophils, basophils, neutrophils and activated lymphocytes during a "late-phase" allergic reaction.

The significance of the late-phase reaction has been substantiated by studies using pharmacologic modulators. Drugs that inhibit the late-phase reaction (e.g., corticosteroids, cromolyn sodium) have been observed to induce clinical remission by reducing inflammation and bronchial hyperactivity. In contrast, drugs that are effective only for the inhibition of an immediate (or "early-phase") allergic reaction only, do not appear to affect the course of the chronic disease.

Misoprostol, a PGE analogue, has been shown to have similar immunomodulatory effects as the parent compound, prostaglandin E, in some experiments. Molecularly, misoprostol consists of four individually characterized isomers. Its molecular structure includes an =OH on carbon 9 and an alpha-OH on carbon 11 of the cyclopentane ring of the structure. The action of misoprostol as a gastro-protective agent in experimental animals has been observed by several investigators. Because of this particular protective action, misoprostol has been approved for use in the prevention of gastric mucosal ulcers associated with nonsteroidal anti-inflammatory drugs (NSAIDS) in high risk patients. However, the cellular mechanism by which misoprostol provides this gastro-protective action remains uncertain.

Misoprostol has been described as having an action profile similar to that of the corticosteroids. Misoprostol has also been characterized as being essentially free of therapeutic activity other than in the gastrointestinal tract. This particular agent may not be prescribed for administration to reproductively active women because of its known deleterious physiological effects during pregnancy. Administered orally, misoprostol is also known to cause diarrhea in a significant percentage of patients. Misoprostol is also known by the name CYTOTEC®.

Misoprostol has not been investigated or described as having anti-allergy activity. However, studies presented herein by the inventors demonstrate that according to the inventive method described by the inventors, misoprostol may be employed in inhibiting that condition characterized during the "late-phase" (i.e., 2–12 hours after initial allergen exposure) of a cutaneous allergic reaction. These results are most surprising and unexpected, as misoprostol has such a short half-life and because the "late phase" of an allergic reaction until 2 to 12 hours after exposure to an allergen.

Misoprostol, at concentrations of $10^{-8}$ to $10^{-4}$ M, has also been found by the present inventors to inhibit histamine release from basophils in vitro. Previous studies with PGE have demonstrated an inhibitory effect on basophils at similar concentration.

Cytokines and interleukins play an important role in the induction of inflammation. Activation of T cells and macrophages by foreign antigens leads to the synthesis of various cytokines including the interleukins (IL 1–IL 11), CSFs (colony stimulating factor), TNF (tumor necrosis factor) and the interferons. The interleukins and cytokines have diverse biological effects. For example, IL 1 activates T cells, B cells, granulocytes and many other tissue cells. In addition, many cytokines are known to have a potent pro-allergic action in vivo.

The inventors have shown that IL3 and GM-CSF activate basophils and cause histamine release. The present inventors have also described a group of cytokines called histamine releasing factors (HRF). HRF has also been shown to correlate with the severity of bronchial asthma. Immunotherapy has been observed to cause a reduction in the synthesis of HRF. Some studies have demonstrated the inhibition of IL 5 activity (by administering anti-IL 5 antibody) will prevent eosinophilic inflammation.

The present inventors have recently described a group of cytokines called histamine release inhibitory (HRIF) that block cytokine-induced mediator release from basophils. One species of HRIF appears to be identical to IL 8. IL 8 has been shown to inhibit histamine release by HRF, CTAPIII and IL3. The present inventors postulate that given the results presented herein, a network of cytokines may be functioning to modulate the function of basophils.

An important pro-inflammatory mechanism of action of cytokines is their induction of adhesion molecules on endothelium and leukocytes. For example, IL 1, TNF, GM-CSF and IFN-gamma are strong inducers of the expression of adhesion molecules. Endothelial cells also express a series of adhesion molecules, including intercellular adhesion molecules (ICAM) 1 and 2, endothelial leukocyte adhesion molecules (ELAM) 1, endoCAM (CD31), vascular cell adhesion molecule (VCAM) 1, and GMP 140. These molecules are instrumental in directing the traffic of the inflammatory cell to the target tissue.

Granulocytes, lymphocytes and monocytes also express a series of adhesion molecules that are ligands/receptors for endothelial cell counterparts. The migration of lymphocytes is mediated by a number of homing receptors such as CD44 (hermes antigen), leukocyte adhesion molecule (LAM)1, and integrins (e.g., VLA 4,5, and 6, LFA-1 (CD11a/CD18)).

The integrins are one of a group of molecules involved in granulocyte emigration from the blood vessels. Other molecules that have this activity include LFA-1 (CD11a/CD18), MAC-1 (CD11b/CD18), gp 150/95 (CD11c/CD18), ICAM-1, GMP 140 and others. Leukocyte adhesion molecules are unregulated by cytokines such as IL 1, TNF, IFN-gamma and GM-CSF, and inflammatory mediators such as platelet activating factor (PAF). The effect of prostaglandins and misoprostol on the expression of adhesion molecules on endothelium and inflammatory cells is unknown.

An allergy is generally recognized as a hypersensitivity to the exposure of a particular agent or substance, termed an "allergen." Allergies may be classified as immediate and delayed, and include atopy, serum sickness, allergic drug reactions, contact dermatitis, urticaria, asthma, allergic rhinitis and anaphylactic shock. Allergies are principally manifest in the gastrointestinal tract, the skin, the respiratory tract, and the cardiovascular system (e.g. during anaphylactic shock). Contact dermatitis is an example of a type IV hypersensitive reaction of the skin produced by contact with a chemical substance having the properties of an antigen or a hapten.

Typically, an allergic reaction may be divided into an early phase and a late phase. An early-phase allergic reaction typically takes place within 15-30 minutes after exposure to an allergen. Typical symptoms are shortness of breath, bronchospasm, soft tissue swelling, edema, hypotension, itching, redness of the skin, wheezing, nausea, vomiting, diarrhea, cramps, and, in some cases, shock. Symptoms usually resolve spontaneously after treatment. Mediators of early allergic reaction by way of example include histamine, leukotrienes, platelet activating factor, and kinins. These mediators are released primarily by mast cells and basophils. The treatment of the early phase reaction typically includes use of antihistamines, cromolyn sodium and beta-adrenergic drugs. The late phase reaction is a late phase sequela of the early reaction, and takes place 3-12 hours later. It is caused by mediators secreted by many inflammatory cells including eosinophils, basophils, monocytes, lymphocytes, and neutrophils. This type of reaction is clinically more relevant, since it correlates better with the clinical severity of the diseased state, such as with the disease, asthma. Late-phase allergic reactions are also generally more painful than early-phase allergic reactions. Treatment for these maladies typically includes administration of corticosteroids and cromolyn sodium.

Asthma is also a form of allergic reaction which is characterized by the release of histamine and other inflammatory mediators in the pulmonary tissue. Asthma typically results in impaired breathing capacity. One particular example of a delayed or "late-phase" (terms used interchangeably in the present invention) allergic reaction is observed in the cutaneous skin allergic response to the antigen of dust mites.

Corticosteroids are highly effective drugs for treatment of asthma and other allergic disease, but they have a multitude of serious side effects which include osteoporosis, obesity hypertension, cataracts, gastric ulcer reactivation of tuberculosis, delayed bone healing, predisposition to infection and adrenal insufficiency.

A method or agent for inhibiting late-phase allergic reactions, particularly late-phase allergic cutaneous reactions and respiratory related allergic maladies, without corticosteroids, would provide an improvement in the clinical management of late-phase allergic reactions.

SUMMARY OF THE INVENTION

The present invention provides effective pharmaceutical compositions and methods for treating and preventing a variety of late-phase allergic reactions, particularly those of a cutaneous and potentially respiratory involvement.

In a particularly preferred embodiment, the method provides for inhibiting or preventing a late-phase allergic response to an allergen in an animal comprising treating the animal with a pharmacologically effective dose of misoprostol in a pharmaceutically acceptable excipient. The method may thus be conveniently employed for treating and preventing late-phase allergic reaction to virtually any antigen.

In a most particularly preferred embodiment, the method provides for the inhibition of late-phase cutaneous response to a dust mite allergen. When utilized for inhibiting late-phase allergic reaction to dust mite allergen, the pharmacologically effective concentration of misoprostol is between about 100 $\mu$g to about 400 $\mu$g total dose (average 1-6 $\mu$g/kg body weight) in tablet form. The most preferred dose of misoprostol in tablet form is 200 $\mu$g (about 3 $\mu$g/kg bodyweight). Such tablets may be prepared with misoprostol employing those standard tableting techniques described in the literature. Most preferably, the method may be employed for inhibiting late-phase cutaneous response to dust mite allergen in humans.

Late-phase cutaneous allergic reactions are also manifest in the condition known as urticaria ("hives"), for which the present methods of treatment and prevention may also be applied.

The misoprostol may be used to inhibit such late-phase allergic cutaneous reactions in animals which manifest 2, 3, 4 or 5 hours after cutaneous exposure to dust mite antigen.

In a most preferred embodiment of the method, misoprostol is prepared in a formulation suitable for parenteral, oral, topical, intranasal, or aerosol administration to an animal. As formulated for topical application, the misoprostol-containing preparation may be applied to an allergic cutaneous area (i.e., the skin area which has responded with an allergic reaction upon contact with an allergen) to provide a therapeutic treatment to a late phase cutaneous allergic response. As a topical treatment for a cutaneous late-phase allergic response, misoprostol is to be formulated together in a pharmaceutically acceptable excipient at a concentration of between about 200 µg to about 5 mg.

As the present inventors have found that misoprostol has inhibiting activity for basophil histamine release, and have demonstrated the effectiveness of its use in inhibiting late-phase allergic reactions, particularly late-phase cutaneous allergic response to dust mite, the inventors propose a method for treating other conditions characterized at least in part by the release of histamine or other physiological allergic mediators from basophils. Such conditions include respiratory late-phase allergic reactions, such as asthma and allergic rhinitis. Thus, a method for treating asthma in an animal is also proposed by the inventors.

The method for treating respiratory late-phase allergic disorders in an animal, according to a most particularly preferred embodiment of the invention, comprises identifying an animal having an allergen-related impairment of breathing capacity, treating the identified animal with a pharmacologically effective dose of misoprostol (capable of inhibiting late phase allergic reaction), and continuing administration of the misoprostol until the animal evidences an improved breathing capacity.

Most preferably, the method is employed for the treatment of late-phase respiratory allergic reaction (e.g. asthma and allergic rhinitis) formulated as an aerosol. Methods for preparing a pharmacological agent in a form suitable for safe administration to a human patient or to any animal are known to those of skill in the pharmaceutical arts. As an aerosol, the pharmacologically effective dose of misoprostol capable of inhibiting late-phase allergic response would preferably be between about a 25 µg and a 800 µg total dose.

As a method for treating asthma, it is proposed that the above described doses of misprostol in a suitable pharmaceutically acceptable excipient formulated for administration as an aerosol would provide a therapeutically beneficial treatment for humans with asthma or allergic rhinitis. While the most preferred mode of administrating the pharmacologically effective dose of misprostol is through an aerosol preparation for the treatment of asthma, the misoprostol may also potentially be formulated in tablet and administered to the patient orally to provide an effective treatment for allergic reactions.

By way of example, allergens which may be involved in late-phase allergic response to an allergen, such as in late-phase cutaneous allergic reaction or allergen-related impairment of breathing capacity, include pollen, mold, dust mites, trees, grass, weeds, food allergens, animal dander, chemicals, occupational antigens, etc.

In an even more particularly preferred embodiment of the invention, a method is provided for inhibiting histamine release by basophils. In one embodiment, this method comprises treating a basophil, a culture of basophils or a tissue containing basophils with a pharmacologically effective dose of misoprostol. A pharmacologically effective dose of misoprostol effective for inhibiting histamine released by basophils in vitro is defined as a concentration between about $10^{-8}$ to $10^{-4}$ M.

It is hypothesized that the present methods would also provide an effective method for treating and preventing other physiological conditions which are characterized by allergen-stimulated release of an allergic mediator (such as histamine), from the population of cells known as basophils and mast cells, such as allergic rhinitis and asthma.

As used in the present description of the invention, a late phase allergic reaction-inhibiting concentration of misoprostol may be prepared in a variety of pharmaceutically acceptable excipients which provide a formulation suitable for administration to an animal which is non-toxic. By way of example, an excipient of choice for formulating misoprostol for topical application as a relatively viscus liquid or cream-like preparation.

In still another embodiment of the claimed invention, an anti-allergy pharmaceutical agent capable of inhibiting late phase allergic reaction in an animal is provided. Accordingly to one particularly preferred embodiment of the claimed pharmaceutical anti-allergy agent, the present invention provides an anti-allergy agent comprising a concentration of misoprostol in a pharmaceutically acceptable excipient capable of inhibiting late-phase cutaneous allergic response in an animal. For this most preferred embodiment, the anti-allergy pharmaceutical agent is prepared in a formulation suitable for application as a topical treatment. In such form, the concentration of misoprostol is between about 200 µg/ml and 5 mg/ml.

The particular pharmaceutical anti-allergy agent of the present invention may be administered as a treatment through any of a variety of means, those most particularly preferred modes of administration being parenterally, by inhalation, topically, orally or intranasally.

A variety of aerosol, tablet, or liquid forms of the pharmaceutical anti-allergy agent may be formulated for administration to a patients using those tableting, aerosol formulation suspension techniques and parenteral formulation preparation protocols known to those in the art of pharmaceutical preparations to provide non-toxic therapeutic agents for human administration.

For purposes of the present description of the invention, the phrase "late-phase" allergic response is defined as an allergic response to an allergen manifest at least 2 hours after exposure to a particular allergen, for example 2 hours after a cutaneous exposure to dust mite allergen.

In the examples presented by the inventors herein, histamine and codeine were employed as positive controls for the early phase cutaneous reaction in the present studies.

A number of abbreviations are used throughout the present specification. These abbreviations include:
PMA = Phorbol Myristate Acetate
Con A = Concanavalin A
IgE = immunoglobulin E
HRF = histamine releasing factor
AU/ml = allergy unit per milliliter.
mcg = microgram

BRIEF DESCRIPTION OF THE FIGURES

FIG. 1. The effect of misoprostol on the cutaneous response to dust mite allergens. Six allergic patients underwent intradermal skin testing with 50 AU/ml of dust mite allergens on two different days with or without prior medication with misoprostol (200 µg). The mean wheal diameter was read at 15 min (immediate allergic reaction), 1 hour and then hourly for 5 hours (late allergic reaction). Asterisks indicate statistical significance as determined by Wilcoxon's signed rank test for paired samples (P<0.05).

DESCRIPTION OF THE PREFERRED EMBODIMENTS

The invention described herein demonstrates novel and particularly efficacious methods and agents for the treatment of late phase allergic reactions in a patient. The method provides relief from the painful symptoms typically attendant a late phase allergic reaction without the risk of a variety of side affects typically attendant the employ of currently available corticosteroid therapeutic treatments.

Misoprostol in tablet form (200 μg tablet) was obtained as CYTOTEC ® (from G. D. Searle and Co). Anti IgE was obtained Boehringer Scientific. Dust mite was obtained from Hollister-Stier. Codeine phosphate and histamine phosphate were obtained from Sigma Chemical.

The following examples are presented only to describe preferred embodiments and utilities of the present invention, and to satisfy best mode requirements. The examples are not meant to limit the scope of the present invention unless specifically indicated otherwise in the claims appended hereto.

EXAMPLE 1

Basophil Histamine Release

The present example is presented to demonstrate the utility of using misoprostol in the treatment of histamine release-related allergic physiological responses in vivo. The present example also demonstrates the potential utility of the use of misoprostol with the claimed method and treatment in inhibiting release of allergic reaction mediators.

1. Histamine Release Test

The effect of misoprostol on histamine release from basophils was studied. Histamine release was induced with anti-IgE and mononuclear cell-derived histamine releasing factor (HRF). Anti-IgE was chosen because its mechanism of histamine release is similar to that of a standard allergen. HRF is a representative cytokine.

Leukocytes were isolated by sedimentation with 1.5% hydroxyethyl starch in the presence of 0.01 M EDTA as an anticoagulant. The washed leukocytes were suspended in HACM (10 mM Hepes buffer, pH 7.4, containing 137 mM NaCl, 5 mM KCl, 0.03% human serum albumin, 2 mM $CaCl_2$ and 1 mM $MgCl_2$). Aliquots of 50 μl of leukocyte suspension were preincubated with various concentrations of misoprostol ($10^{-8}$ to $10^{-4}$ M) for 10 min at 37° C., and then challenged with 50 μl of a predetermined concentration of anti-IgE and HRF for an additional 45 min at 37° C. Three sets of controls were run simultaneously: 1) cells preincubated with buffer and then challenged with secretagogues, 2) cells preincubated with misoprostol and then challenged with buffer, and 3) cells preincubated with buffer and challenged with buffer. Each experiment was done in duplicate.

At the conclusion of the incubation, supernatant was separated from the cells by centrifugation at 600×g for 5 min at 4° C. and the histamine content of the supernatants were measured using an automated fluorometric analyzer. The total histamine content of the cells was measured by lysing the cells with 3% perchloric acid. The percentage of histamine release was calculated according to the formula:

$$\text{Histamine in the supernatant} \times \frac{100}{\text{Total Histamine in the Cells}}$$

Spontaneous histamine release from the cells was subtracted from the calculated histamine release.

2. Results

Figure 4:
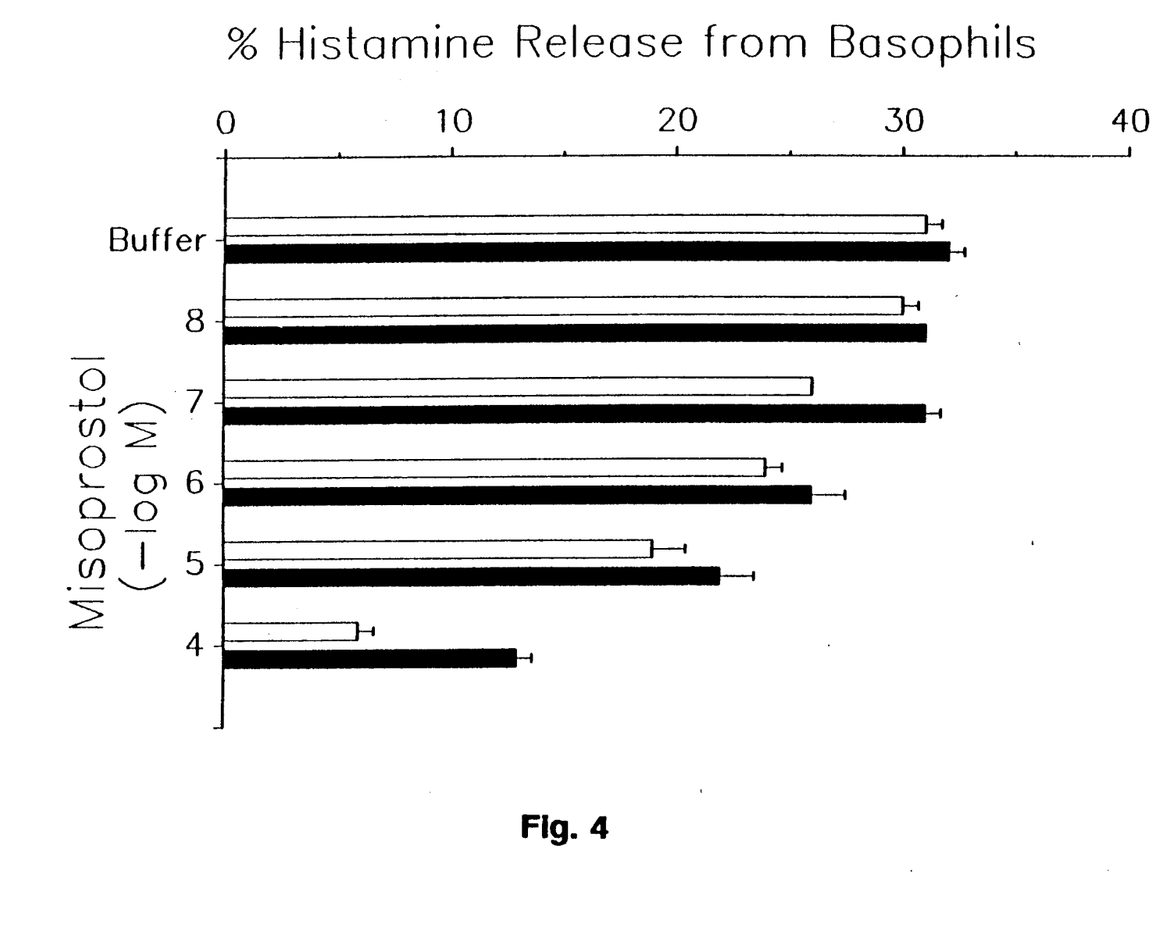
FIG. 4. The effect of misoprostol on anti-IgE- and histamine releasing factor (HRF)-induced histamine release from leukocytes. Peripheral blood leukocytes from three allergic donors were preincubated with buffer or misoprostol ($10^{-8}$ to $10^{-4}$ M) for 10 min at 37° C. and then challenged with anti-IgE (1:1000 dilutions of antiserum) or HRF. The cells were incubated for another 45 min and the released histamine was measured spectrofluorometrically. Total cellular histamine was measured after lysis of the cells with 3% perchloric acid. The results of one of three typical experiments are shown.

In three experiments, misoprostol inhibited both anti-IgE- and HRF-induced histamine release from leukocytes in a dose-dependent manner at high concentrations (FIG. 4). The maximal inhibition was observed at $10^{-4}$ M. In further studies, the inhibition of anti-IgE-induced histamine release was carried out by preincubating basophils with misoprostol for different periods of time (5, 10, 15, 30 min) and at different temperatures (22° and 37° C.). The optimal preincubation time and temperature were found to be 10 min and 37° C. respectively.

EXAMPLE 2

Inhibition of Neutrophil Beta-Glucuronidase Release

The present example is presented to demonstrate the activity of misoprostol for inhibiting the secretion of a major granular enzyme, beta glucuronidase, from an inflammatory cell type known as neutrophils. Neutrophils are an important cell type involved in the inflammatory response. The results also demonstrate that misoprostol can inhibit neutrophils and/or the inflammatory response of neutrophils (release of a granular enzyme).

1. Beta Glucuronidase Release Test

The test was carried out according to Schroeder et al.[23] Briefly, leukocytes were separated from peripheral blood obtained from ten donors by sedimentation with hydroxyethyl starch. The buffy coat was washed and processed in HACM buffer.

Aliquots of cells were sequentially incubated with various concentrations of misoprostol ($10^{-8}$ to $10^{-4}$ M) or buffer for 15 minutes and then with cytochalasin B (500 µg/ml) for 10 minutes. The C5a (1 µg/ml) was added and the incubation continued for 30 minutes at 37° C. The tubes were centrifuged and 100 µl of supernatants was transferred to wells of an ELISA plate containing 100 µl of 0.01 M p-nitrophenyl-B-D-glucuronide in 0.1 M sodium acetate, pH 4.

The ELISA plate was incubated 18 hours at 37° C. 200 µl of 0.4 M glycine buffer, pH 10, was added at the conclusion, and the plate read by an ELISA reader at 546 nm. The results will be expressed as percentage release of beta-glucuronidase by C5a in the presence of misoprostol with reference to the release in the presence of buffer.

Leukocytes were thus preincubated with various concentrations of misoprostol and then challenged with C5a. The released beta-glucuronidase was assayed by its ability to metabolize p-nitrophenyl-B-D-glucuronide.

2. Results

In three experiments, C5a induced the release of beta-glucuronidase from neutrophils in a dose dependent manner, and the optimal concentration for release was 1 µg/ml. The mean beta-glucuronidase release was $19 \pm 3\%$. Misoprostol was used in one experiment, and it inhibited C5a-induced enzyme release in a dose-dependent manner. The maximal inhibition was 48% at $10^{-5}$ M concentration.

EXAMPLE 3

Cutaneous Allergic Reaction with Misoprostol

The present study demonstrates the effectiveness of misoprostol in a method for treating and preventing late-phase allergic reactions, most particularly late-phase allergic cutaneous reactions. Misoprostol was administered as an oral tablet.

The serum level of misoprostol after an oral dose of 200 µg was found to be 300-600 pg/ml ($\sim 1-2 \times 10^{-9}$ M). While the half life of misoprostol is between about 1.5 to 1.7 hours, the present study demonstrated effective inhibition of late-phase cutaneous allergic reaction to dust mite antigen 4-5 hours after exposure. This indicated to the inventors that the mechanism of action of misoprostol is different from the mere inhibition of histamine release from basophils. The inventors' observation that misoprostol does not affect immediate allergic reactions (i.e. "early-phase"), also indicates that misoprostol does not function simply to inhibit histamine release from basophils. It is postulated that misoprostol is acting at a very early phase of inflammation, since it is eliminated from the body long before the peak of a late-phase allergic reaction.

The same pharmacological activity is expected by the present inventors from topical application of misoprostol, such as, for example, when administered as a cream or ointment in association with liposomes.

1. Patients

Six patients with known skin test allergic reactivity to dust mite (*Dermatophagoides pteronyssinus/farinae*) were studied. All patients had an initial intradermal testing with the allergen to determine the dose that evoked a late-phase cutaneous response. Patients were asked to withhold medications. Patients were required to follow the following guidelines in the use of drugs that are known to modulate skin reactivity: short-acting antihistamines must be stopped for 72 hours, and tricyclic antidepressants and benzodiaxepines for two weeks. Patients on astemizole and systemic steroid were excluded. Any patient with a history of recent narcotic drug intake or having taken an investigational drug within one month of the study was excluded. Other exclusion criteria include skin infections or skin disorders, history of anaphylaxis, and history of systemic or moderate-severe localized reactions to histamine, codeine, or allergen extract, and patients with systemic illnesses requiring uninterrupted medication.

2. Skin Testing Procedure

After an overnight fast, patients had intradermal skin testing with dust mite (50 AU/ml), codeine phosphate (1 mg/ml), histamine phosphate (0.275), and a saline control. 50 AU/ml of dust mite had previously been determined by the inventors to induce a late-phase skin reaction in most allergic donors. The longest and perpendicular diameter of the wheal response were read at 15 minutes. The measurement was repeated hourly for 5 hours. Previous experience of the inventors indicated that the peak of the late-phase skin reaction occurred at 4-5 hours following the immediate ("early-phase") reaction.

Three days after an initial treatment, each patient was given a 200 mcg tablet of misoprostol (CYTOTEC ®; G.D. Searle & Co.) after an overnight fast. Thirty minutes later (time of peak blood level following an oral dose in a fasting subject), skin testing was performed as described above. The immediate and late-phase reactions were measured as above.

3. Results

Figure 1:
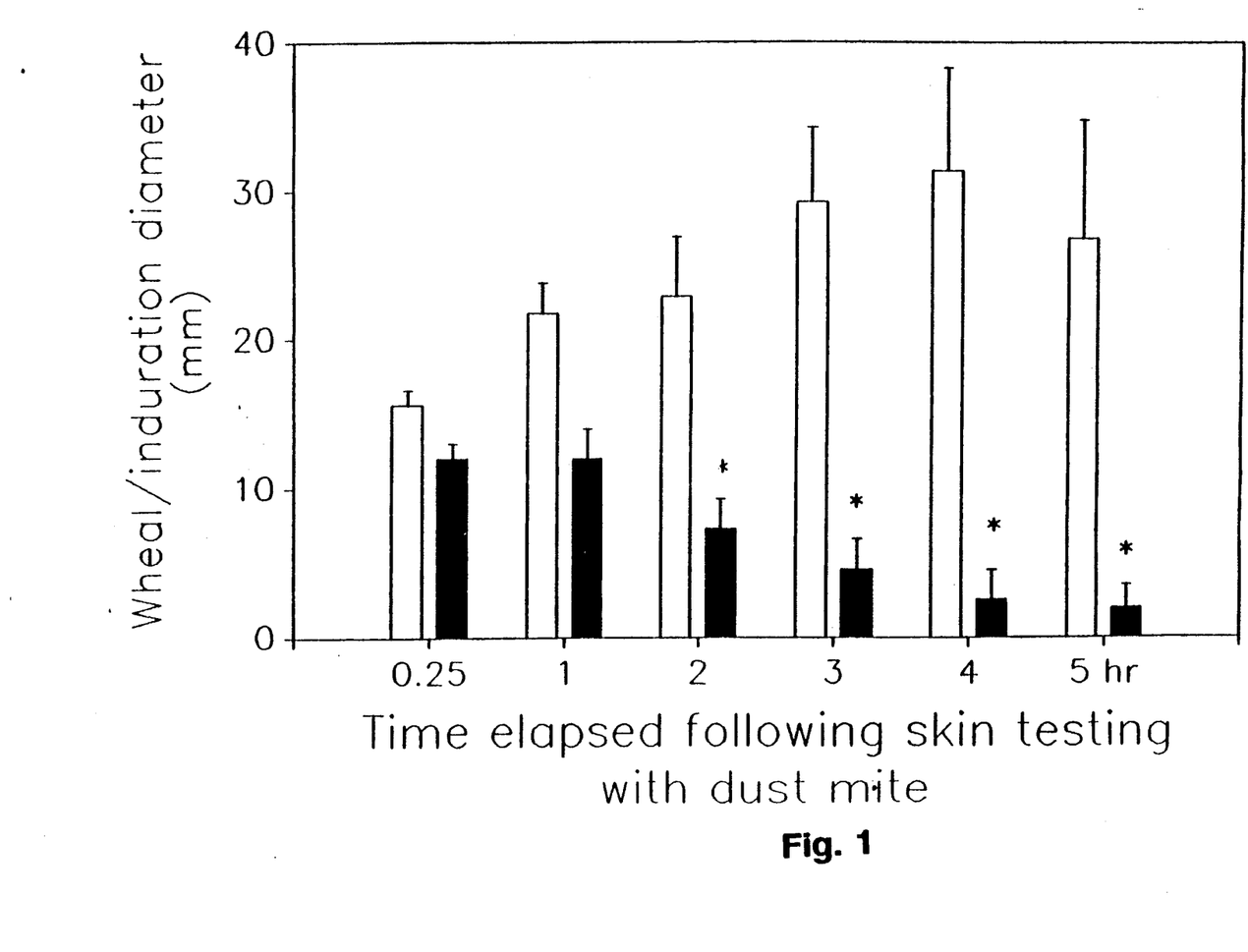
Figure 2:
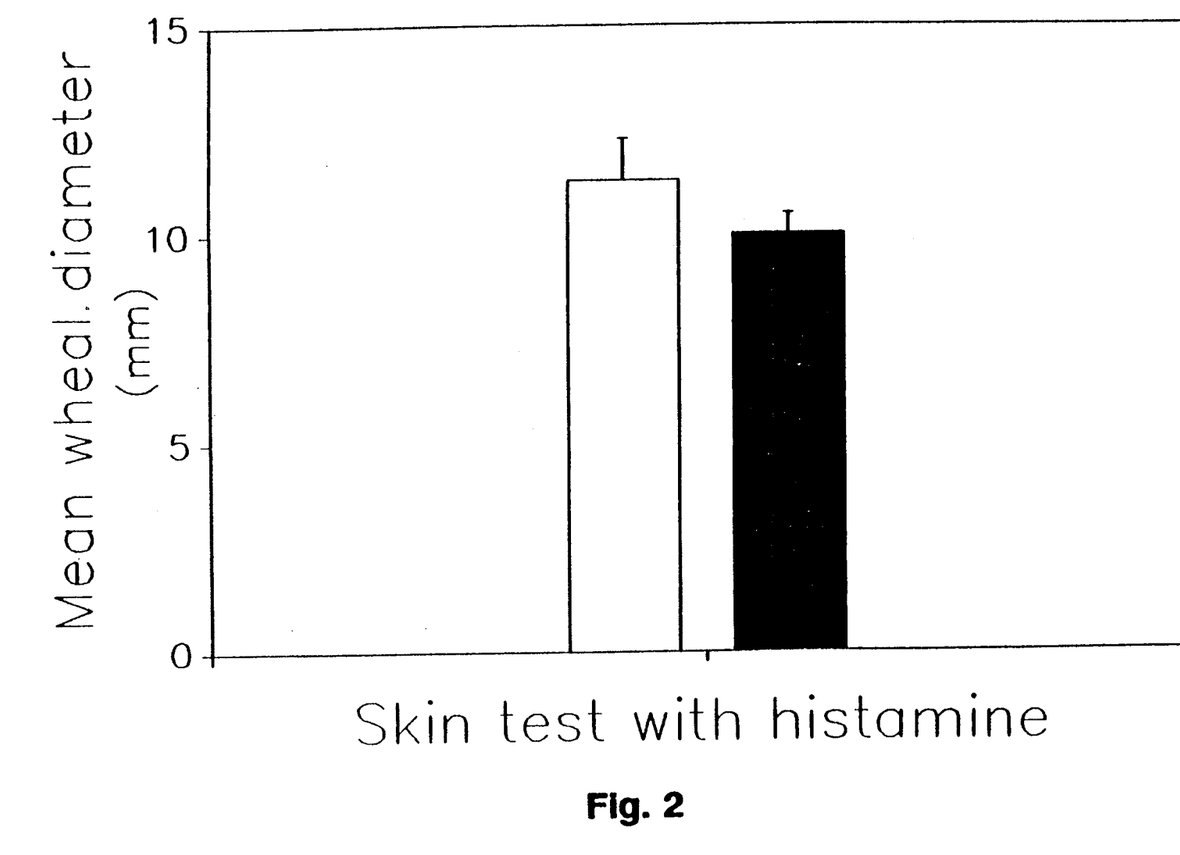
FIG. 2. The effect of misoprostol on the cutaneous response to histamine in six allergic patients as in FIG. 1. Histamine was used as a positive control for skin reactivity. The histamine-induced wheal response disappeared within 30 minutes. There was no statistical difference in the histamine-induced wheal response after misoprostol administration.
Figure 3:
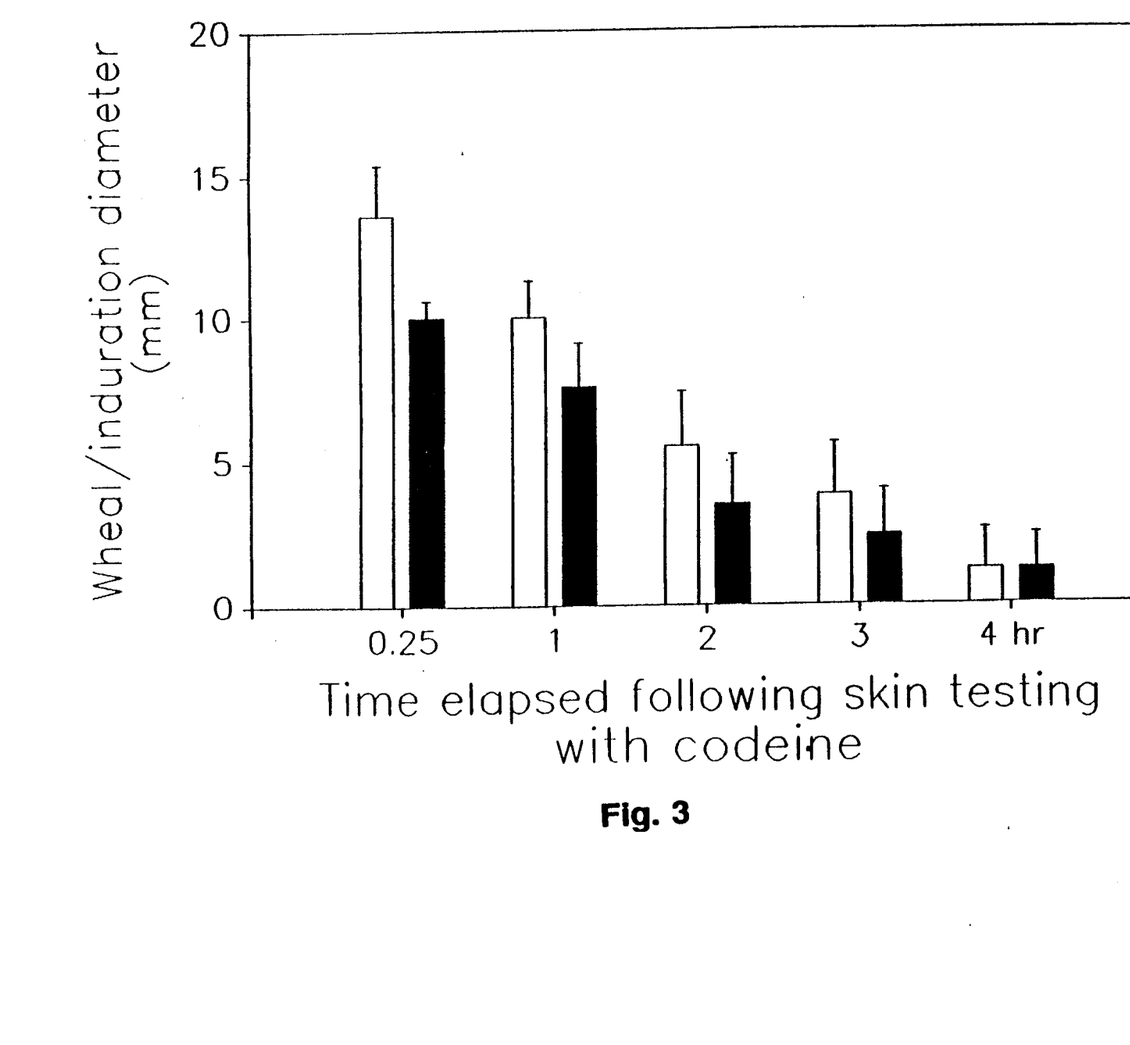
FIG. 3. The effect of misoprostol on the codeine-induced skin reaction in six allergic patients as in FIG. 1. Codeine was used as a positive control for mast cell reactivity. There was no statistical difference in the codeine-induced wheal response after misoprostol administration.

The allergic reaction to skin testing is presented as the mean of the longest and the perpendicular diameters. All six patients developed an immediate allergic reaction at 15 min (FIG. 1). The wheal response to histamine (FIG. 2) and codeine (FIG. 3) subsided after the immediate phase, although the codeine-induced response cleared more slowly. In contrast, the reaction to dust mite continued to increase in intensity and reached its plateau at 4 hours. Administration of misoprostol did not affect the immediate phase allergic reaction, but it significantly prevented the protracted late-phase reaction. There was no effect of misoprostol on codeine- and histamine-induced immediate allergic reaction.

EXAMPLE 4

Misoprostol and Cutaneous Late-Phase Allergic Reaction Double Blind Placebo Control Study The present example presents clinical data collected from 12 adult males and females. Females who participated in the study were reproductively incompetent, as they either had undergone a tubal ligation or hysterectomy.

STUDY PROTOCOL AND RESULTS

1. Cutaneous Challenge Study

A. Patients

Twelve patients with known skin test reactivity to dust mite (*Dermatophagoides pteronyssinus/farinae*) were studied. All patients had an initial intradermal testing with the allergen to determine the dose that evokes a late cutaneous response. Patients were asked to withhold medications. The following guidelines were maintained for drugs that are known to modulate skin reactivity: short-acting antihistamines must be stopped for 72 hours, and tricyclic antidepressants and benzodiazepines for two weeks. Patients on astemizole and systemic steroid were excluded. Any subject with a history of recent narcotic drug intake or having taken an investigational drug within one month of the study was to be excluded. Other exclusion criteria included skin infections or skin disorders, history of anaphylaxis, and history of systemic or moderate-severe localized reactions to histamine, codeine, or allergen extract, and patients with systemic illnesses requiring uninterrupted medication.

The study was conducted in a double-blind placebo-controlled manner. Placebo and misoprostol (200 μg) were put in look-alike capsules. The capsules were stored by one of the investigators who did not see the patients. On the study day, the coded capsule containing the placebo or the active drug was given to the nurse in a blinded fashion. The coded capsule was then administered to the patient. The patient was also blinded as the content of the capsule. The skin testing procedure was conducted 30 minutes later. The procedure was repeated 5 days later. Each patient received either placebo on 1 day or misoprostol on another day.

B. Skin Testing Procedure

Each patient had intradermal skin testing with dust mite (50 AU/ml), codeine phosphate (1 mg/ml), histamine phosphate (0.275 mg/ml), and a saline control. The present inventors had previously determined that 50 AU/ml of dust mite induced a late-phase skin reaction in most allergic donors. The longest and perpendicular diameter of the wheal response were read at 15 minutes. The measurement was repeated at 1 hour and hourly for 5 hours. Previous experience of the inventors indicated that the peak of the late-phase skin allergic reaction occurred at 4-5 hours following the immediate reaction.

C. Results

Figure 5:
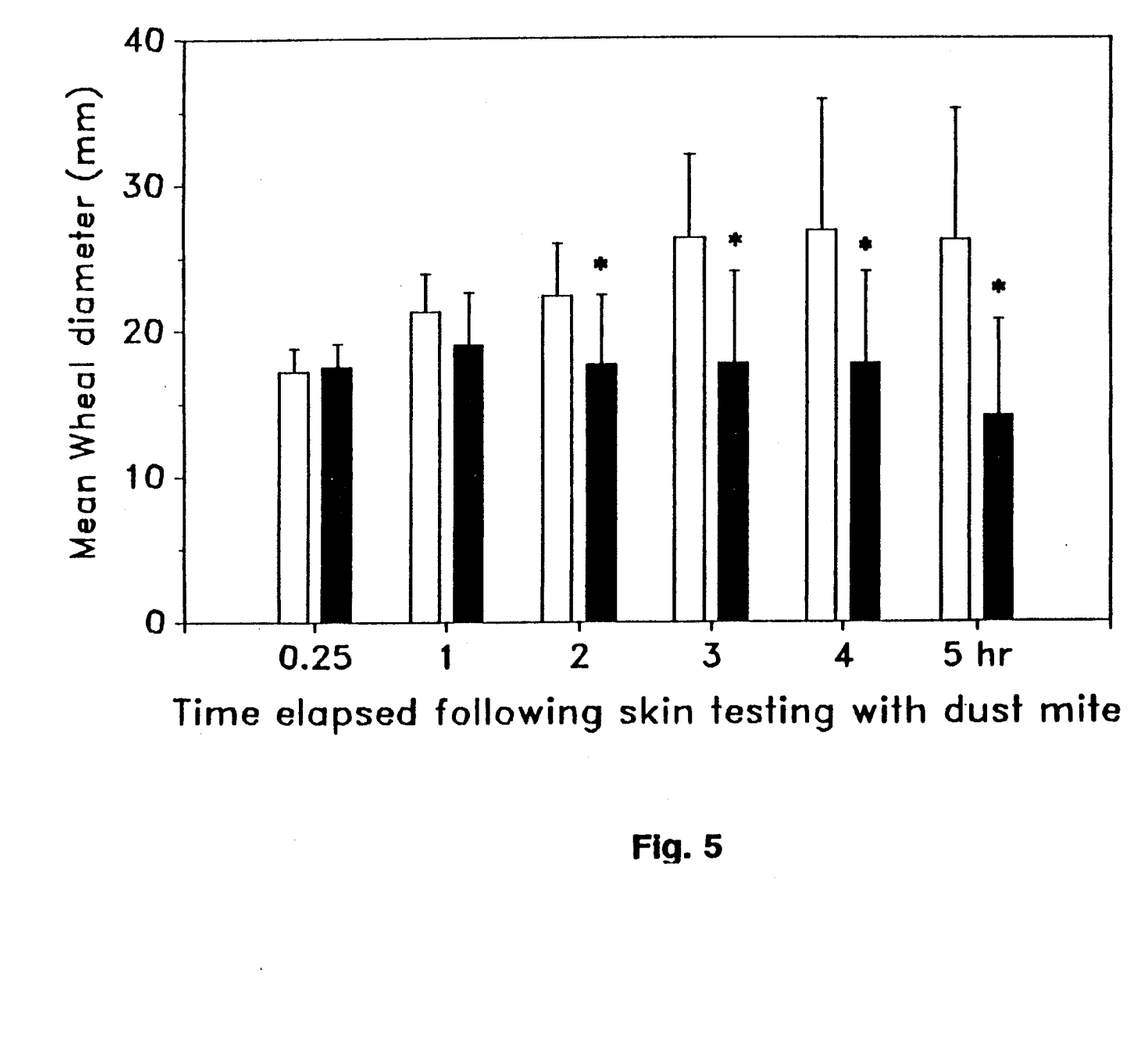
FIG. 5. The effect of misoprostol and placebo on cutaneous allergic response to dust mite allergens. Twelve allergic patients underwent intradermal skin testing with 50 AU/ml of dust mite allergens on two different days after receiving misoprostol (200 μg) or placebo in double-blind placebo-controlled fashion. The mean wheal diameter was read at 15 min (immediate early-phase cutaneous allergic reaction), 1 hour and then hourly for 5 hours (late allergic reaction). Asterisks indicate statistical significance as determined by Wilcoxon's signed rank test for paired samples (P<0.05).
Figure 6:
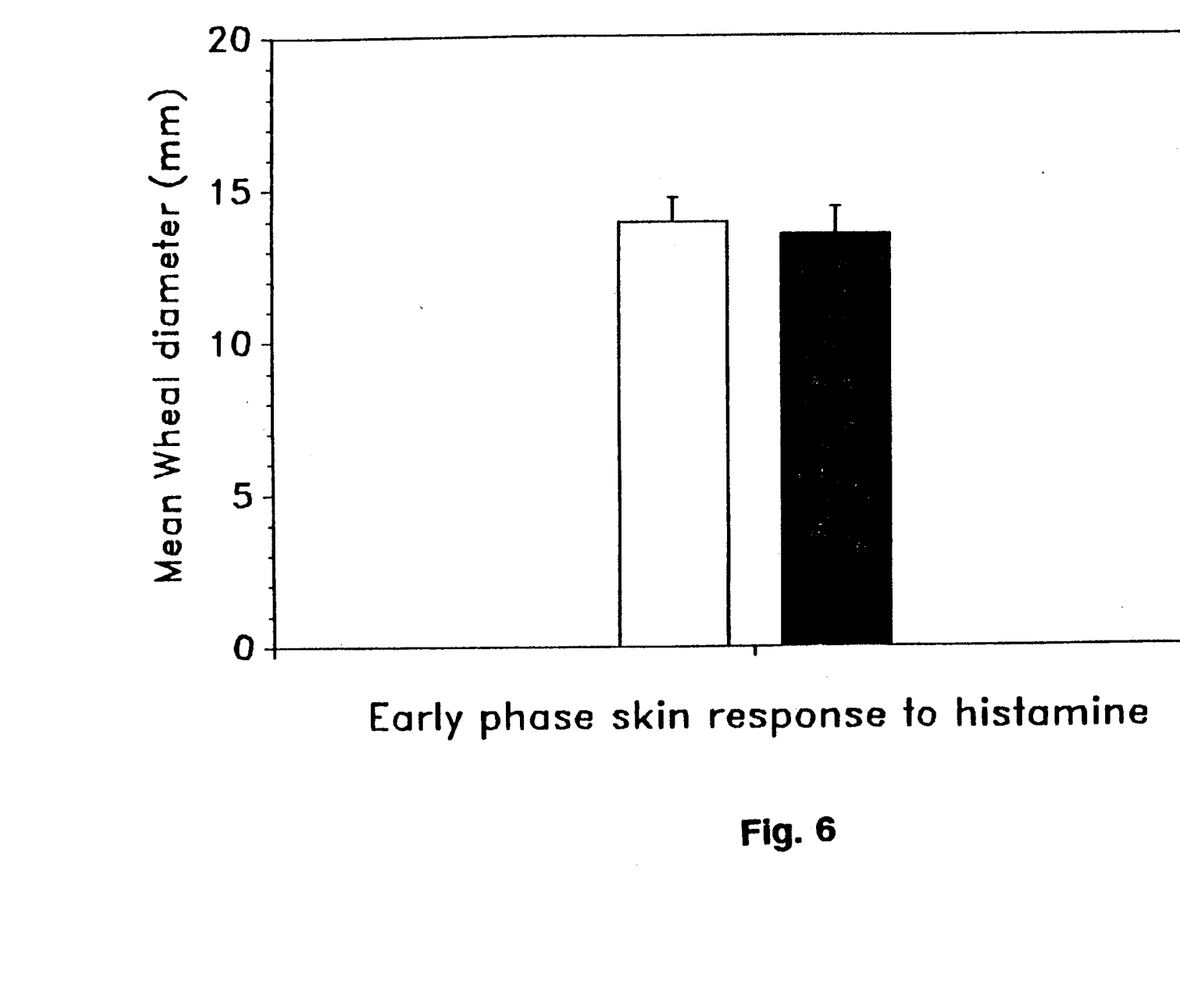
FIG. 6. The effect of misoprostol and placebo on the cutaneous response to histamine in twelve allergic patients as in FIG. 5. Histamine was used as a positive control for skin reactivity. The histamine-induced wheal response disappeared within 30 minutes. There was no statistical difference in the histamine-induced wheal response after misoprostol administration (P>0.05).
Figure 7:
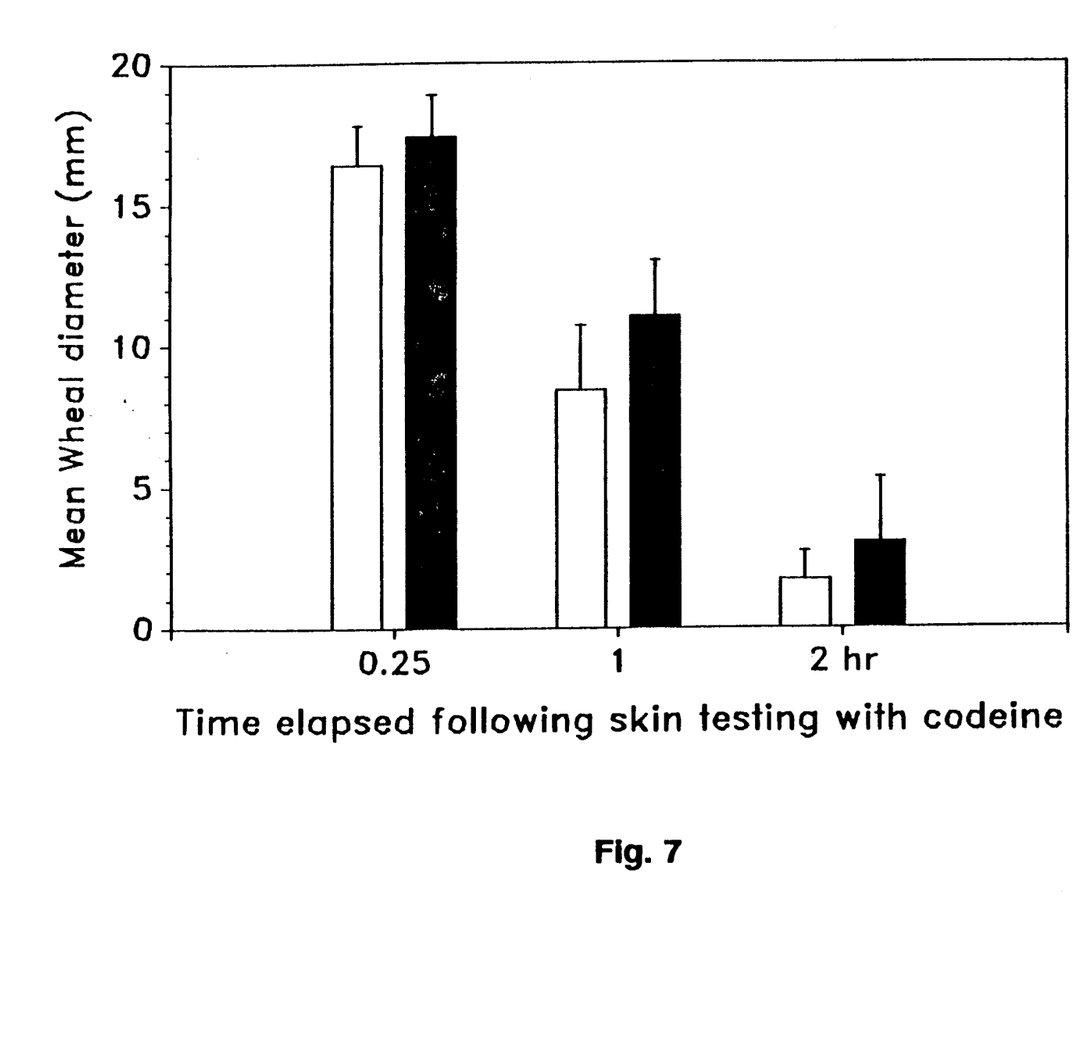
FIG. 7. The effect of misoprostol and placebo on the codeine-induced skin reaction in twelve allergic patients as in FIG. 5. Codeine was used as a positive control for mast cell reactivity. There was no statistical difference in the codeine-induced wheal response after misoprostol administration (P>0.05).

The allergic reaction to skin testing is presented as the mean of the longest and the perpendicular diameters. All twelve patients developed an immediate allergic reaction at 15 minutes (FIG. 5). The reaction to dust mite continued to increase in intensity and reached its plateau at 4 hours on the placebo day. Administration of misoprostol did not affect the immediate phase allergic reaction, but it significantly ($P<0.05$) inhibited the protracted late-phase reaction. There was no effect of misoprostol on histamine- and codeine-induced allergic reactions (FIGS. 6 and 7, respectively).

PROPHETIC EXAMPLE 5

Proposed Therapeutic Use of Misoprostol in Nasal Allergic Reactions

The present example is provided to demonstrate the utility of misoprostol in the treatment of nasal immediate and late allergic reactions in humans.

1. Study Design

The effect of misoprostol on nasal immediate and late allergic reactions will be investigated on 20 patients in a double-blind placebo-controlled randomized study. Misoprostol or placebo (lactose) will be administered in look-alike coded capsules 30 minutes before the nasal challenge. The same coded drug will be given again 6 hours later. Symptom score will be monitored every 30 minutes until the immediate reaction, and then hourly for 12 hours. The second challenge will be conducted within 5-7 days. Nasal challenges will be conducted at the same time of the day to avoid changes in the bioresponse due to the diurnal rhythm.

Procedure

Nasal antigen challenges will be performed on allergic patients as described by Naclerio et al. Initially patients will be challenged with the diluent using a spray that delivers 0.2 ml each squirt. Symptoms will be monitored for 30 minutes. Then 0.2 ml of a predetermined dose of the appropriate allergen will be delivered into each nostril at increasing doses at 30 minutes intervals, and symptoms monitored. Patients will be evaluated for their response with reference to a symptom score well known to those of skill in the art.

Patients will be evaluated for their response with reference to a symptom score, well known to those of skill in the art. The symptom score for three cardinal symptoms is calculated the following way: sneezes 0 (none), 1 (1-8 sneezes/hr), 2 (9-16/hr), and 3 (>16/hr); rhinorrhoea and nasal congestion are graded as 0 (none), 1 (mild), 2 (moderate) and 3 (severe). The maximal possible score is 9. Each patient will be asked to record the symptom score hourly for 12 hours on a diary card.

If the symptoms score reaches 6 at any point during the challenge, the next concentration of the allergen will be omitted. However, if the symptom score is between 4 and 6, half of the next concentration will be applied.

With the results obtained from the above described study, effective doses of nasally applied misoprostol may be defined for clinical use in humans.

PROPHETIC EXAMPLE 6

Proposed Therapeutic Use of Misoprostol in Respiratory Allergic Reactions

The present example is provided to outline the proposed utility of misoprostol in the treatment of respiratory late-phase allergic reactions in humans. Such respiratory late-phase allergic reactions are involved in, for example, asthma and allergic rhinitis.

The effect of misoprostol on allergic bronchial asthma can be studied using the existing formulation as, for example, using a 200 mcg tablet of misoprostol such as that obtainable from Cytotec ®(G. D. Searle, Inc.). The dosing regimen is 1 tablet every 6 hours. The clinical efficacy of the drug can be studied in a number of ways, including the measurement of reduction in daily symptom score (shortness of breath, wheezing, and cough), reduction in the usage of bronchodilators (albuterol inhaler or others) and improvement in peak expiratory flow rates and other spirometric indices as well as in bronchial hyperreactivity.

Another possibility is the intrabronchial delivery of the drug in lipid emulsions as an aerosol. Misoprostol will be dissolved in soybean oil (200 µg/ml) and then incorporated in a lipid emulsion (final concentration 20 µg/ml). This emulsion will be aerosolized using a standard nebulizer. The drug will be delivered at a dose of 3-5 µg/minutes for 5 minutes. Patients will be treated with the aerosol treatment every 6 hours. The clinical efficacy will be monitored as described above.

Still another possibility would be to administer the misoprostol as a nasal aerosol, for example in the treatment of allergic rhinitis, as described in Example 5.

1. Study Design

Twenty allergic asthmatic patients will be recruited for this double-blind placebo-controlled study. Allergen challenge will be conducted on two separate days one week apart. The inclusion criteria include 80% of the previously best recorded FEV1 and FVC on the day of the study. Patients will have a baseline spirometry. Qualifying patients will receive misoprostol or placebo in coded capsules in a randomized fashion. Thirty minutes later the patient will undergo allergen challenge test. After an initial saline inhalation test, the patient will be challenged with a predetermined dose of a skin test-positive allergen extract. Spirometry will be repeated at 5, 10, 15, 30 min, 1 hour and then hourly for 10 hours. All patients will receive another dose of the same coded capsule 6 hours after the initial dose. The study will be repeated one week later.

Bronchial challenges will be conducted at the same time of the day to avoid changes in the bioresponse due to the diurnal rhythm.

Procedure

Patients will have a baseline spirometry in the morning of the study day and then inhale 5 breathes of saline from a DeVilbiss 646 nebulizer connected to a Rosenthal-French nebulization dosimeter, both apparatus being well known to those of skill in the art. Compressed air is passed through the dosimeter for nebulization. Spirometry is repeated at 5 and 15 minutes. If no significant drop in FEV1 (20% fall is considered significant) is noticed, patient will proceed to have allergen challenge with a predetermined dose of a skin test positive allergen. The same nebulizer system will be used for the allergen challenge. Patients will be allowed to take inhaled bronchodilators if they experience even only moderate respiratory distress. For severe respiratory distress, 0.3 ml of epinephrine sc, bronchodilators via nebulizer and theophylline IV will be started and the study discontinued.

Topical administration of misoprostol into the nose and lungs may also be considered. This may include aerosolization of the drug through a metered dose inhaler or through a nebulizer.

The concentration of allergen administered to the patient will be increased until the FEV1 (forced expiratory volume in 1 second) falls 20%.

3. Data Analysis

The results of in vitro study will be analyzed for statistical significance of difference between samples treated with misoprostol and with placebo or buffer in each group. The codes for the blinded drugs for in vivo studies will be deciphered after completion. The results of cutaneous (mean wheal diameter), nasal (symptom score) and bronchial response (FEV1) from the misoprostol day will be compared with that from the placebo day. The statistical significance of differences will be analyzed using Wilcoxon's rank sum test or signed-rank test. All statistical analyses will be considered significant at $P<0.05$.

BIBLIOGRAPHY

The following references are specifically incorporated herein by reference in pertinent part for the purposes indicated.

1. Bauer, RF (1985), Digestive Diseases and Sciences, 30 (11): 118S-125S.
2. Feldman, M (1990) The American Journal of Medical Sciences, 300 (2): 116-132.
3. Dorlands Illustrated Medical Dictionary (19 ), pg. 48-49.
4. Goodman and Gilman, eds., The Pharmacological Basis of Therapeutics, 18th edition (1990), pp. 574-588, pp. 610-611, pp. 618-619, and p. 638.
5. Merck Manual (1987) 14th ed. R. Berkowetal., eds., pp 304-306.
6. Ham EA, Soderman DD, Zanetti ME, et al., (1983) Proc. Natl. Acad. Sci. USA, 60:4349.
7. Marone G, Kagey-Sobotka A, Lichtenstein LM (1979), J. Immunol, 123:1669.
8. Kunkel SL, Chensue SW (1985), Biochem. Biophys, Res. Commun., 128:892.
9. G.D. Searle Investigational Brochure "Arthritis Prostaglandins Research Challenge" page IV-4.
10. Burral BA, Payan DG, Goetzl EJ, in Allergy, Principles and Practice, eds: Middleton E. Reed CE, Ellis EF, Adkinson NF, Yngingrer JW, CV Mosby, St. Louise (1988), pp. 164.
11. Moran M, Mozes MF, Madux MS, et al. (1990), N. Eng. J. Med., 322:1183.
12. Lemanske RF, Jr. Kaliner M (1988), J. Clin. Immunol., 8:1.
13. Alam R, Welter J, Forsythe P, et al. 1989), J. Immunol.; 142.
14. Thueson DO, Speck L, Lett-Brown MA et al. (1979), J. Immunol., 123:626.
15. Alam R, Kuna P, Rozniecki J, Kuzminska B (1987), J. Allergy Clin. Immunol., 79:103.
16. Kuna P, Alam R, Rozniecki J, Kuzminska B (1989), J. Allergy Clin. Immunol., 83:816.
17. Coffman RL, Seymour BWP, Hudak S, et al. (1989), Science, 245:308.
18. Alam R, Grant JA, Lett-brown MA (1988), J. Clin. Invest., 82:2056.
19. Alam R, Forsythe PA, Bodenburg Y, et al. (1991), J. Allergy Clin. Immunol., 87:241.
20. Griffin JD, Spertini O, Ernst TJ et al. (1990), J. Immunol., 145:576.
21. Albelda SM (1991), Am. J. Respir. Cell Mol. Biol., 4:195.

22. Naclerio RM, Meier HL, Kagey-Sobtka A et al. (1985), Am. Rev. Respir. Dis., 131:373.

23. Schroeder J-M, Morwietz U, Morita E, Christophers (1987), J. Immunol., 139:3474.

24. Alam R, Forsythe PA, Lett-Brown MA, Grant JA (1989), J. Immunol., 42:3951.

25. Jaffe EA, Nachman RL, Becker CG et al. (1973), J. Clin. Invest., 52:27.

26. Bochner BS, MacGlashan DW, Jr, Marcotte GV et al. (1990), J. Immunol., 142:3180.

27. Leonard EJ (1987), J. Allergy Clin. Immunol., 79:775.

28. Mizushima et al. (1983), J. Pharm. Pharmacol., 35:397.

29. Middleton, E., et al., Editors (1988), In: Allergy: Principals and Practice, pp. 224-350.

30. Kaliner, M.A., et al. (1987), J.A.M.A., 258:2851.

31. Solley, G.D. et al. (1976), J. Clin. Invest., 58:408.

What is claimed is:

1. A method for inhibiting late-phase allergic response to an allergen in an animal comprising identifying an animal having or at risk of having a late-phase allergic reaction; and inhibiting the late-phase allergic reaction by administering a preparation comprising a pharmacologically effective dose of misoprostol in a pharmaceutically acceptable excipient.

2. The method of claim 1 wherein the late-phase allergic response is a late-phase cutaneous allergic response.

3. The method of claim 1 wherein the animal is a human.

4. The method of claim 1 wherein the late-phase allergic response is a late-phase allergic cutaneous response to a dust mite allergen.

5. The method of claim 2 wherein the late-phase cutaneous response is urticaria or contact dermatitis.

6. The method of claim 1 wherein the allergen is dust mite, grass, mold, chemicals, food allergen, occupational allergen, pollen, weeds or animal dander.

7. The method of claim 1 wherein the misoprostol is administered in tablet form at a dose of between about 100 µg to about 400 µg.

8. The method of claim 1 wherein the misoprostol is administered in a tablet form at a dose of about 200 µg.

9. The method of claim 2 wherein misoprostol is administered as a topical treatment to the allergic cutaneous area contained within a pharmaceutically acceptable excipient at a concentration of between about 200 µg to about 5 mg total dose.

10. The method of claim 1 wherein the late-phase allergic response is a late-phase respiratory allergic response.

11. The method of claim 10 wherein misoprostol is administered as an aerosol at a dose of between about 25 µg and 800 µg.

12. The method of claim 1 wherein the misoprostol may be administered parenterally, orally, topically by inhalation or intranasally.

13. The method of claim 1 wherein the misoprostol is formulated in a liquid suitable for parenteral administration, as a cream or ointment suitable for topical administration, a tablet suitable for oral administration or as an aerosol suitable for inhalation or intranasal administration.

14. A method for treating respiratory late-phase allergic disorder in an animal comprising:
   selecting an animal having a late-phase allergen-related impairment of breathing capacity;
   treating the selected animal with a preparation comprising a pharmacologically effective dose of misoprostol in an amount effective to inhibit late-phase allergic response in the animal; and
   continuing administration of the misoprostol until the animal evidences an improved breathing capacity.

15. The method of claim 14 wherein the pharmacologically effective dose of misoprostol is between about 100 µg and 400 µg in tablet form.

16. The method of claim 14 wherein the misoprostol is administered as an aerosol.

17. The method of claim 16 wherein the pharmacologically effective dose of misoprostol is between about 25 µg to 800 µg in aerosol form.

18. The method of claim 14 wherein the animal is a human.

19. The method of claim 14 wherein the allergen is pollen, mold, grass, dust mite, animal dander, food allergen, chemical, drug or an occupational allergen.

20. The method of claim 14 wherein the pharmacologically effective dose of misoprostol is administered orally, parenterally, or intranasally or by inhalation.

21. The method of claim 14 wherein the respiratory late-phase allergic disorder is allergic rhinitis or asthma.

22. A method for inhibiting histamine release by basophils comprising treating the basophil with a pharmacologically effective dose of misoprostol.

23. The method of claim 22 wherein the pharmacologically effective dose of misoprostol is about $10^{-8}$ to $10^{-4}$ M.

* * * * *